(12) United States Patent
Konishi et al.

(10) Patent No.: US 10,125,406 B2
(45) Date of Patent: Nov. 13, 2018

(54) NOBLE METAL RECOVERY METHOD

(71) Applicant: OSAKA PREFECTURE UNIVERSITY PUBLIC CORPORATION, Sakai-shi, Osaka (JP)

(72) Inventors: Yasuhiro Konishi, Sakai (JP); Norizo Saito, Sakai (JP); Masao Kishida, Sakai (JP)

(73) Assignee: OSAKA PREFECTURE UNIVERSITY PUBLIC CORPORATION, Osaka (JP)

(*) Notice: Subject to any disclaimer, the term of this patent is extended or adjusted under 35 U.S.C. 154(b) by 114 days.

(21) Appl. No.: 15/108,406

(22) PCT Filed: Dec. 28, 2014

(86) PCT No.: PCT/JP2014/084726
§ 371 (c)(1),
(2) Date: Jun. 27, 2016

(87) PCT Pub. No.: WO2015/099189
PCT Pub. Date: Jul. 2, 2015

(65) Prior Publication Data
US 2016/0319394 A1 Nov. 3, 2016

(30) Foreign Application Priority Data
Dec. 28, 2013 (JP) ................................ 2013-273690

(51) Int. Cl.
C12N 1/16 (2006.01)
C22B 3/18 (2006.01)
(Continued)

(52) U.S. Cl.
CPC .................. *C22B 3/18* (2013.01); *C12N 1/16* (2013.01); *C12P 3/00* (2013.01); *C12R 1/645* (2013.01);
(Continued)

(58) Field of Classification Search
CPC ............ C22B 3/18; C22B 11/04; C12R 1/645
See application file for complete search history.

(56) References Cited

U.S. PATENT DOCUMENTS

| 4,690,894 A | 9/1987 | Brierley et al. |
| 2009/0239280 A1 | 9/2009 | De Windt et al. |

FOREIGN PATENT DOCUMENTS

| JP | 11-77008 A | 3/1999 |
| JP | 2003-284556 A | 10/2003 |

(Continued)

OTHER PUBLICATIONS

Narayanan, Kannan Badri et al. "Biological synthesis of metal nanoparticles by microbes." Advances in Colloid and Interface Science vol. 56, pp. 1-13 (Year: 2010).*
(Continued)

*Primary Examiner* — George Wyszomierski
*Assistant Examiner* — Tima M McGuthry-Banks
(74) *Attorney, Agent, or Firm* — Westerman, Hattori, Daniels & Adrian, LLP

(57) ABSTRACT

The present application provides a method to recover noble metal ions by reduction with using yeast. In the method, a liquid containing noble metal ions is provided. An electron donor and yeast are added into the liquid to bring the yeast in contact with the noble metal ions to reduce the noble metal ions. The noble metal can be accumulated in a fungus body of the yeast. The electron donor can be an organic acid, a salt thereof, an alcohol and hydrogen gas.

5 Claims, 8 Drawing Sheets

(51) Int. Cl.
    *C12R 1/645*     (2006.01)
    *C12R 1/865*     (2006.01)
    *C22B 11/00*     (2006.01)
    *C22B 3/00*     (2006.01)
    *C12P 3/00*     (2006.01)

(52) U.S. Cl.
    CPC .............. *C12R 1/865* (2013.01); *C22B 11/04* (2013.01); *Y02P 10/234* (2015.11)

(56) References Cited

FOREIGN PATENT DOCUMENTS

| | | |
|---|---|---|
| JP | 2004-33837 A | 2/2004 |
| JP | 2007-113116 A | 5/2007 |
| JP | 2009-538127 A | 11/2009 |
| JP | 2009-541593 A | 11/2009 |
| JP | 2011-52315 A | 3/2011 |

OTHER PUBLICATIONS

Lin, Zhongyu et al. "Spectroscopic characterization of Au3+ biosorption by waste biomass of *Saccharomyces cerevisiae*." Spectrochimica Acta Part A vol. 61, pp. 761-765 (Year: 2005).*

Sen, Kamalika et al. "Time dependent formation of gold nanoparticles in yeast cells: A comparitive study." Biochemical Engineering Journal vol. 55, pp. 1-6 (Year: 2011).*

Mourato, Ana et al. "Biosynthesis of Crystalline Silver and Gold Nanoparticles by Extremophilic Yeasts." Bioinorganic Chemistry and Applications. vol. 2011, Article ID 546074. 8 pages (Year: 2011).*

Sastry, Murali et al. "Biosynthesis of metal nanoparticles using fungi and actinomycete." Current Science, vol. 85, No. 2. (Year: 2003).*

Breuer, Uta and Hauke, Harms. "Debaryomyces Hansenii—an Extremophilic Yeast with Biotechnological Potential." Yeast, vol. 23 pp. 415-437. John Wiley & Sons, Ltd. onlinelibrary.wiley.com/doi/10.1002/yea.1374/epdf. (Year: 2006).*

Johnston et al., "Gold biomineralization-by a metallophore from a gold-associated microbe", Nature Chemical Biology, Feb. 3, 2013, (5 pages).

Lim et al., "Effect of pH on the Extra Cellular Synthesis of Gold and Silver Nanoparticles by *Saccharomyces cerevisae*", Jouranal of Nanoscience and Nanotechnology, 2011, vol. 11, No. 1, pp. 518-522, (5 pages).

Konishi, "Application of Microbial Biomineralization by Means of Metal-reducing Microorganisms to Fabrication of Noble Metal Nanoparticle Catalysts", Catalyst, Aug. 10, 2013, vol. 55, No. 4, pp. 232-238, (8 pages).

Niide et al., "Yuka Kinzoku Kaishu no Tameno Biomaterial no Kaihatsu", Abstracts of Annual Meeting of the Society of Chemical Engineers, Japan, vol. 75, Feb. 18, 2010, B121, (1 page).

Takahashi et al., "Pan Kobo no Shikiso Oyobi Kinzoku Ion Kyuchaku Tokusei", Kagakukeigaku Kyokai Tohoku Taikai Program Oyobi Koen Yokoshu, vol. 2006, Sep. 22, 2006, p. 149, (1 page).

International Search Report dated Feb. 10, 2015, issued in counterpart International Application No. PCT/JP2014/084726 (2 pages).

Sen et al., "Time dependent formation of gold nanoparticles in yeast cells: A comparative study", Biochemical Engineering Journal, vol. 55, 2011, p. 1-6.

Korobushkina et al., "Nucleation and accumulation of gold in yeast cells", Doklady, Earth Science Sect., vol. 304, 1989, pp. 190-192.

Yazgan et al., "Subcellular distribution of accumulated heavy metals in S, cerevisiae and K. marxianus", 2nd Conference on Advances in Biochemical, 1994, pp. 151-153.

Godlewska-Zylkiewica, "Biosorption of platinum and palladium for their separation/preconcentration prior to graphite furnace atomic absorption spectrometric determination", Spectrochimica Acta, Part B: 2003, pp. 1531-1540.

Extended European Search Report dated Jul. 18, 2017, issued in Patent Application No. 14875501.0 (PCT/JP2014084726).

Das, "Recovery of precious metals through biosorption—A review", Hydrometallurgy, vol. 103, 2010, pp. 180-189.

* cited by examiner

[Fig1]
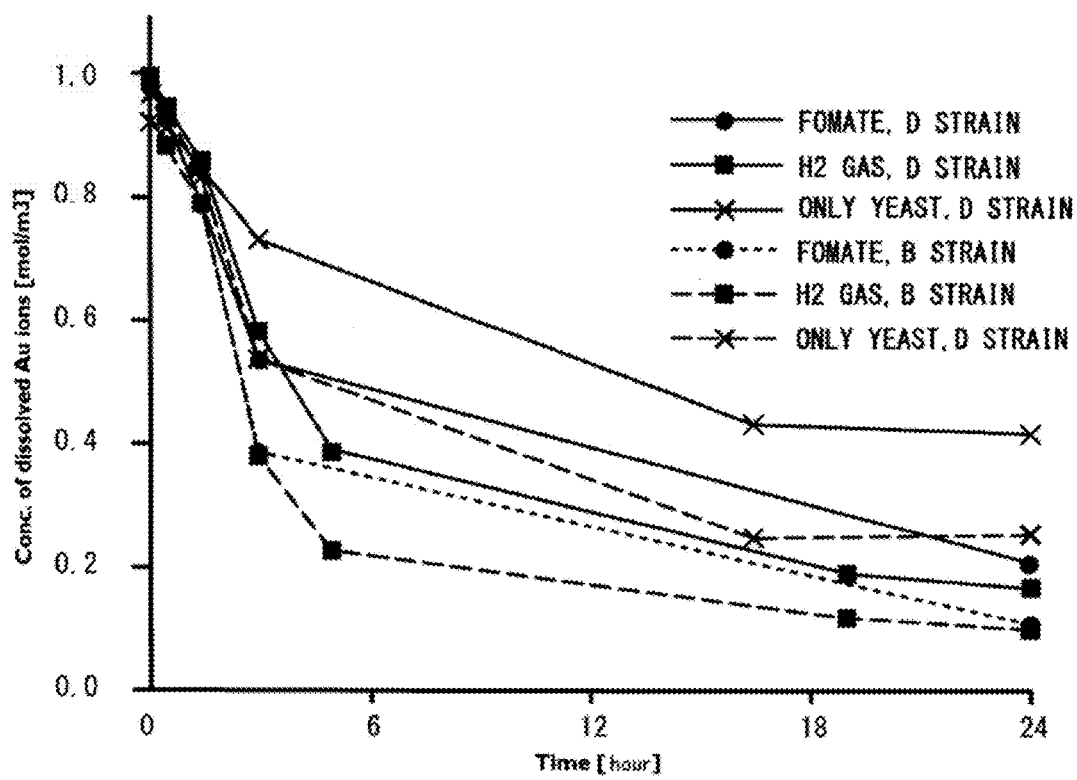
[Fig2]
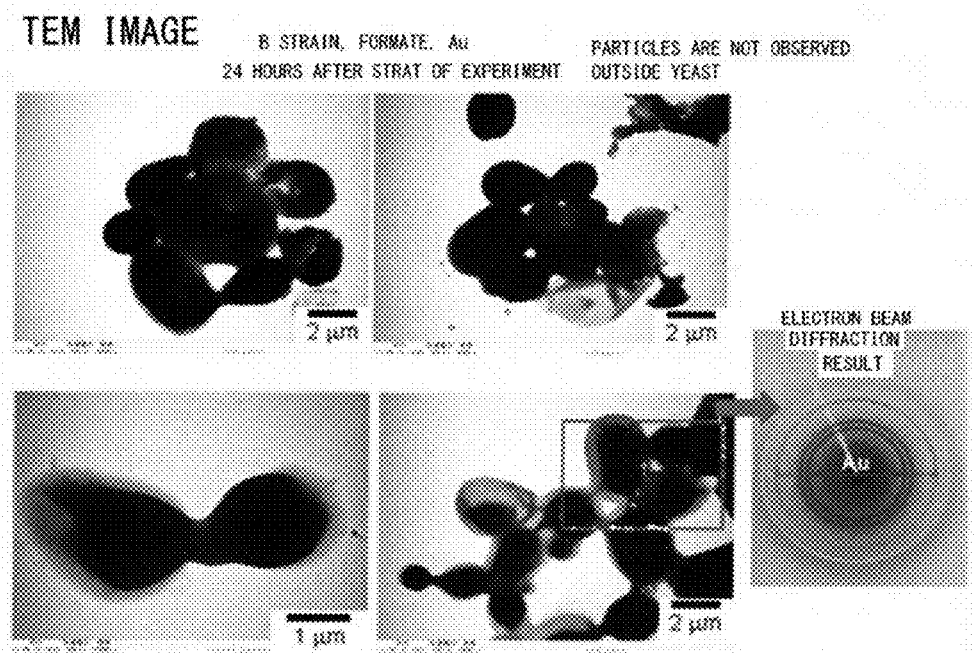

[Fig3]
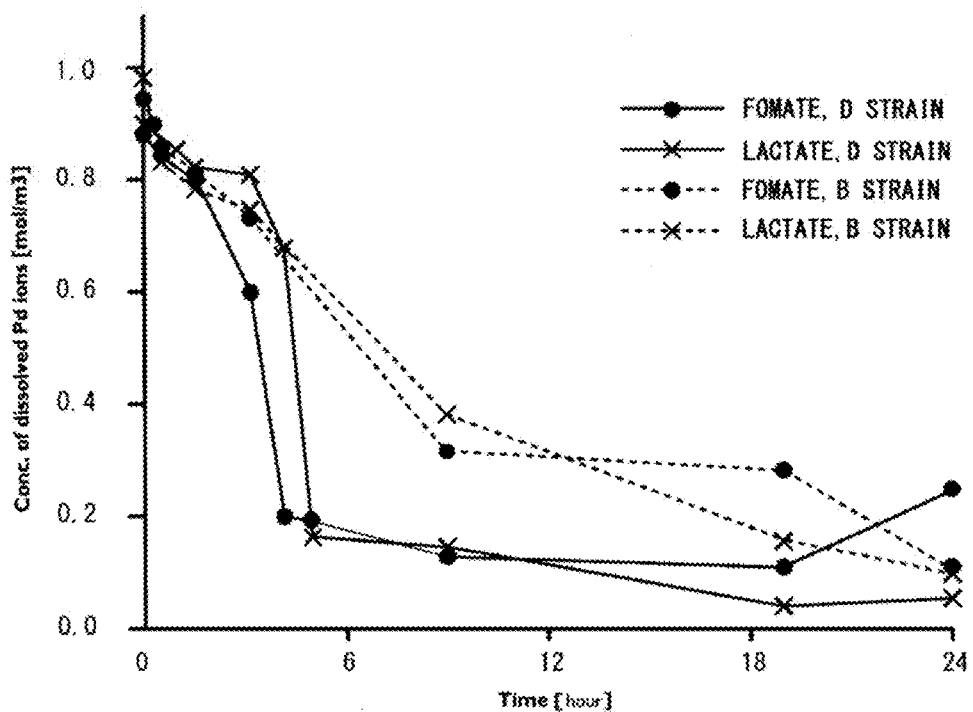
[Fig4]
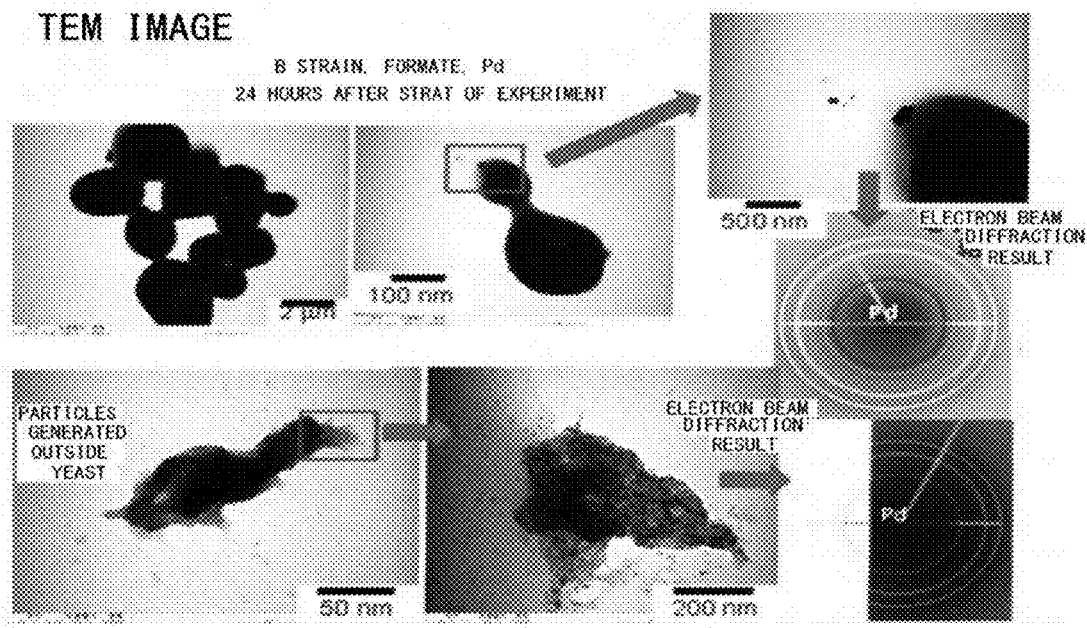

[Fig5]
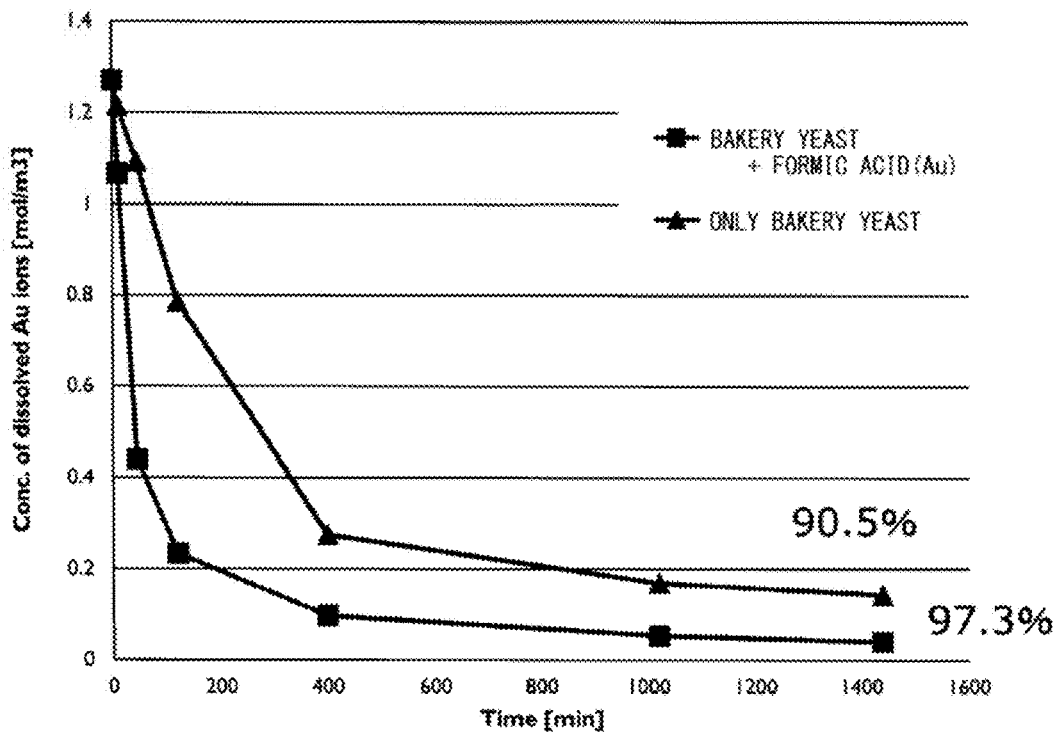
[Fig6]
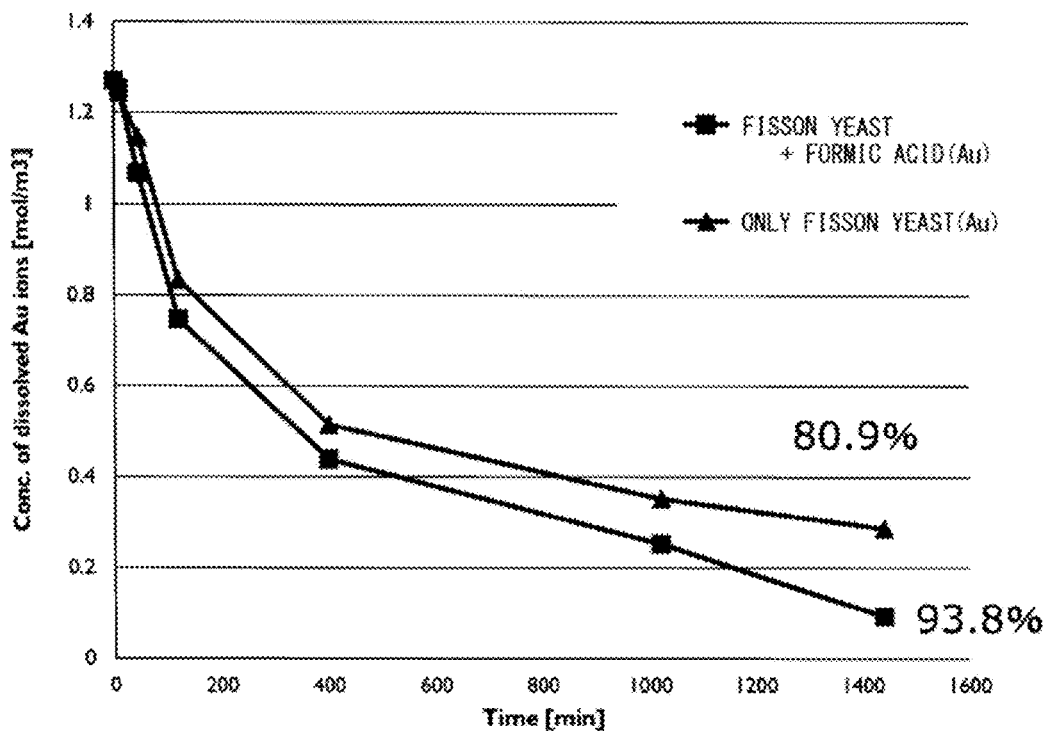

[Fig7]
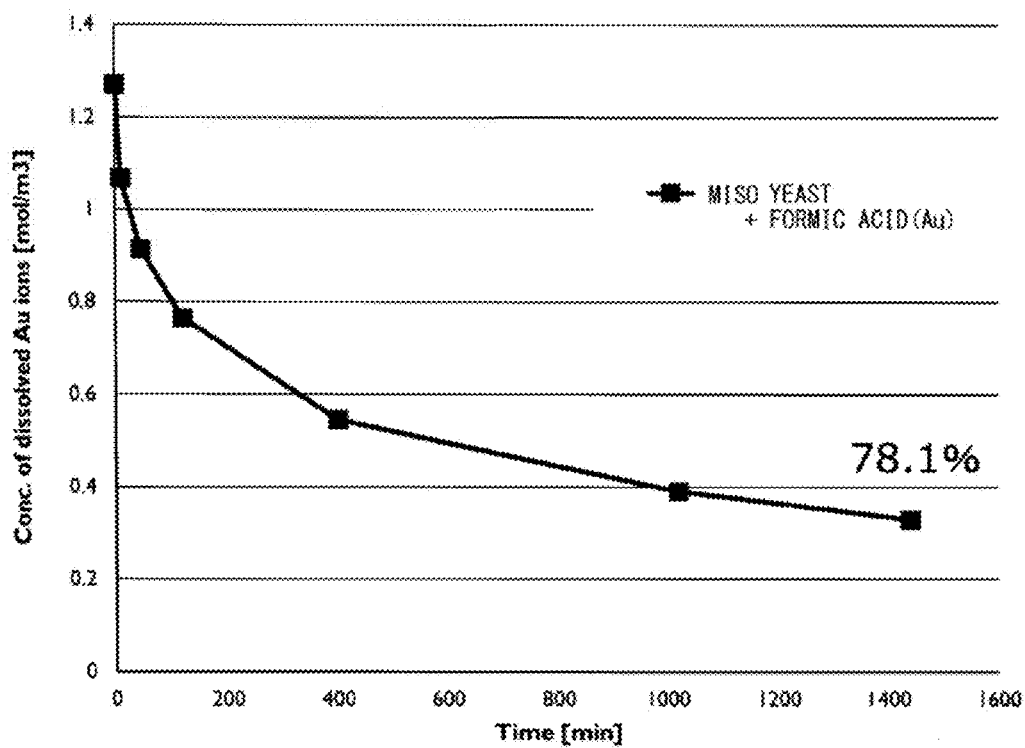
[Fig8]
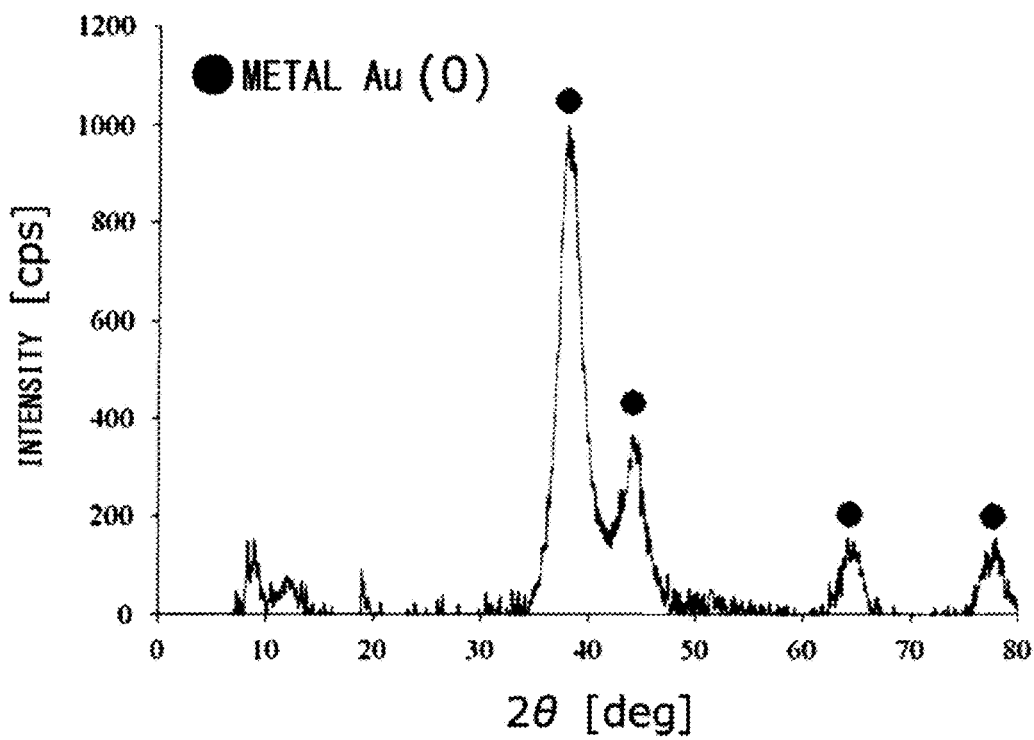

[Fig9]
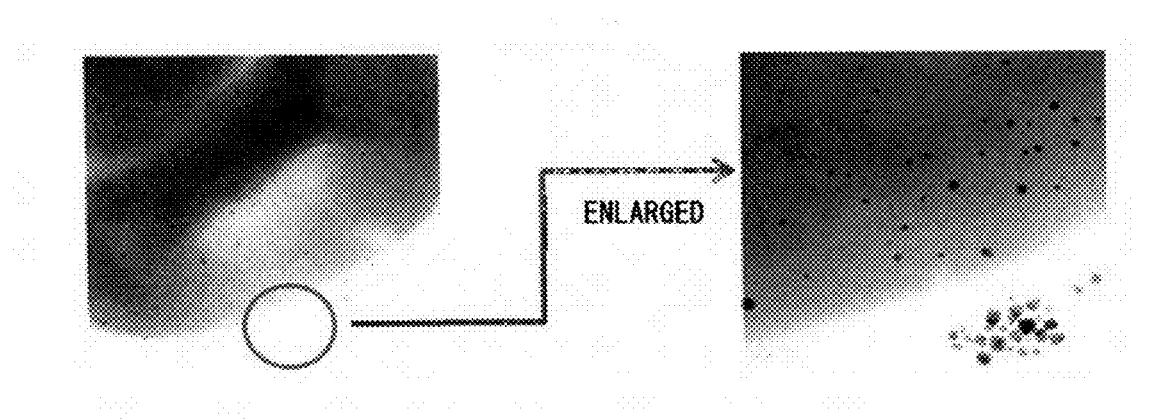
[Fig10]
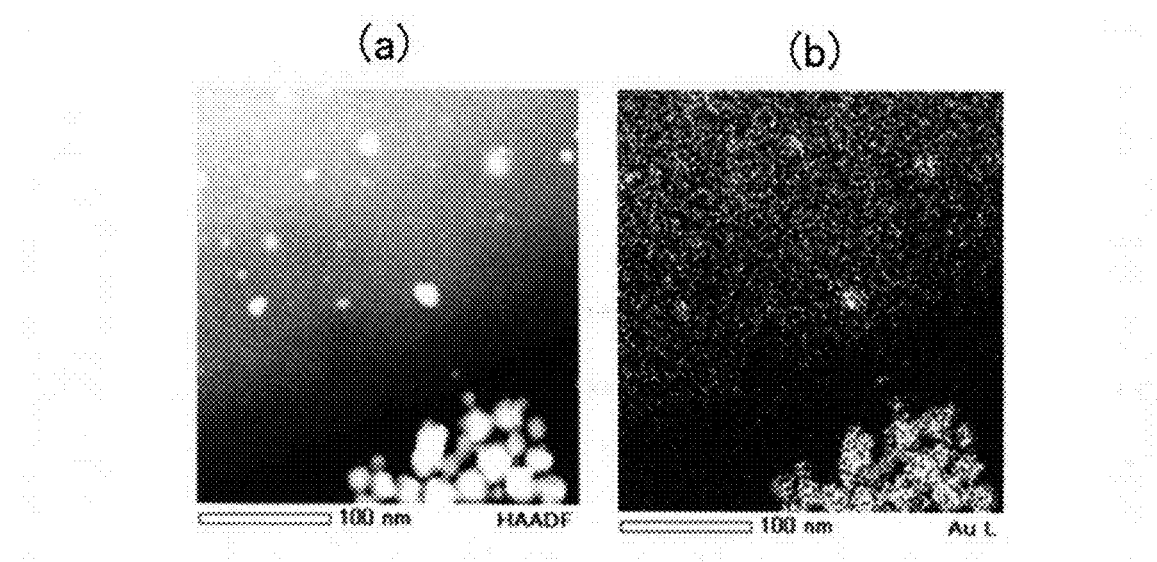

[Fig11]
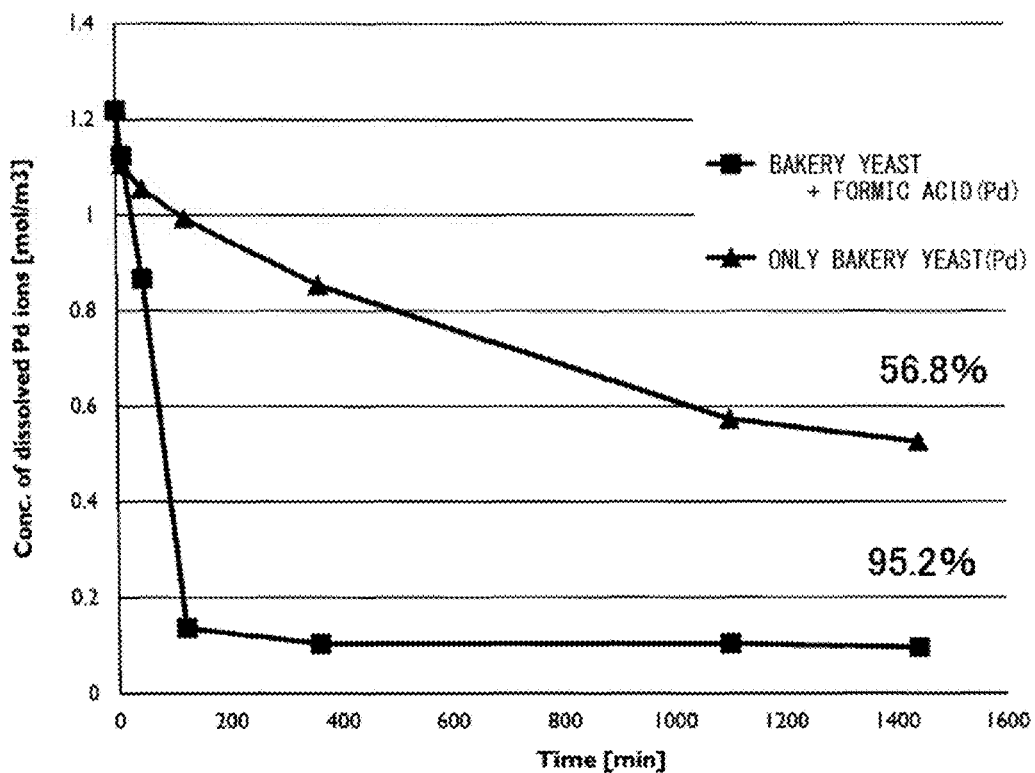
[Fig12]
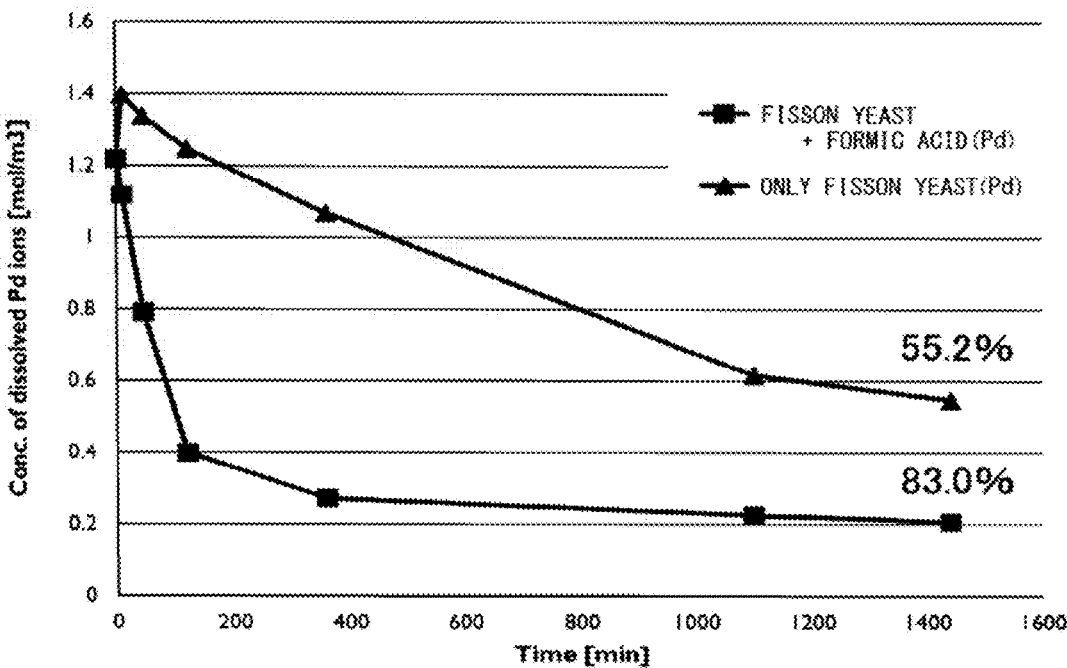

[Fig13]
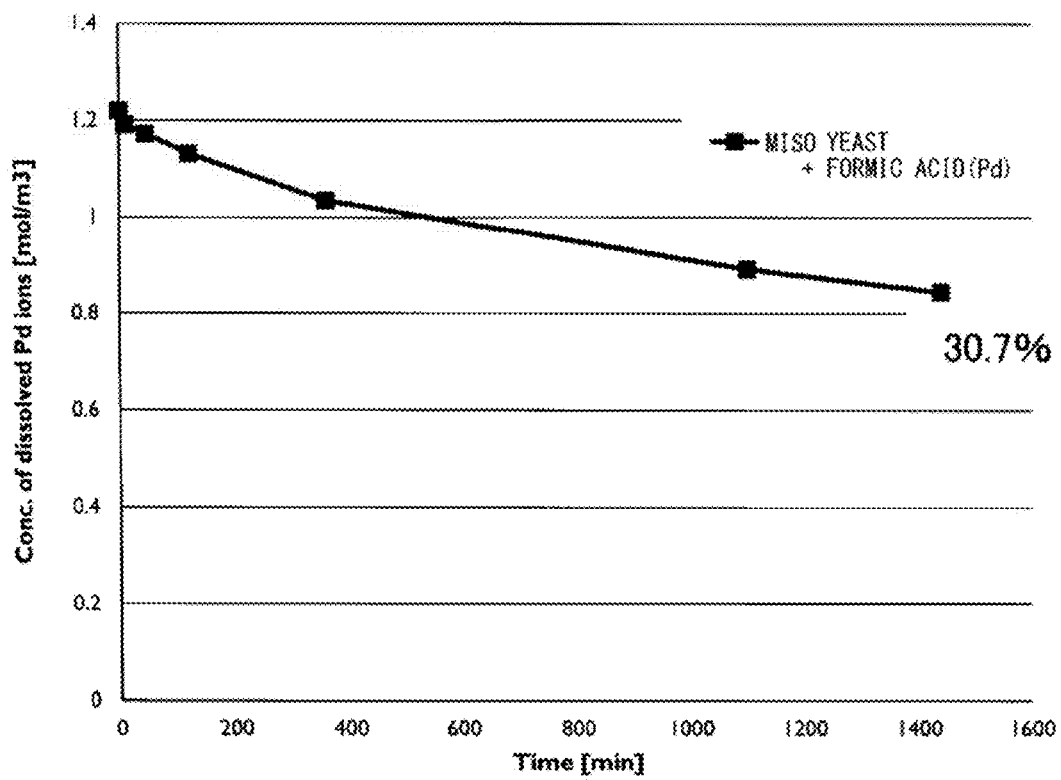
[Fig14]
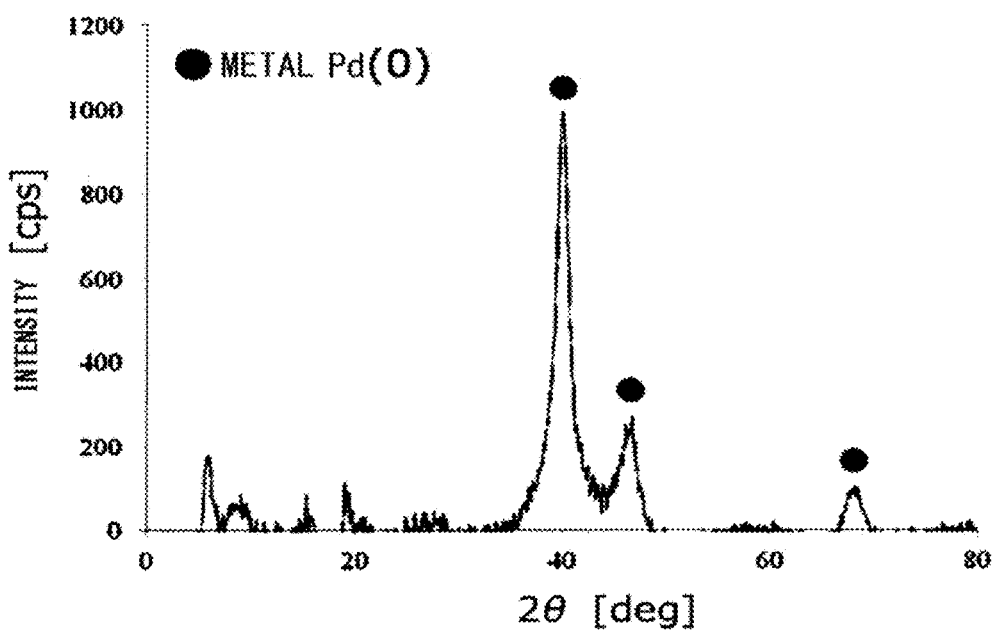

[Fig15]
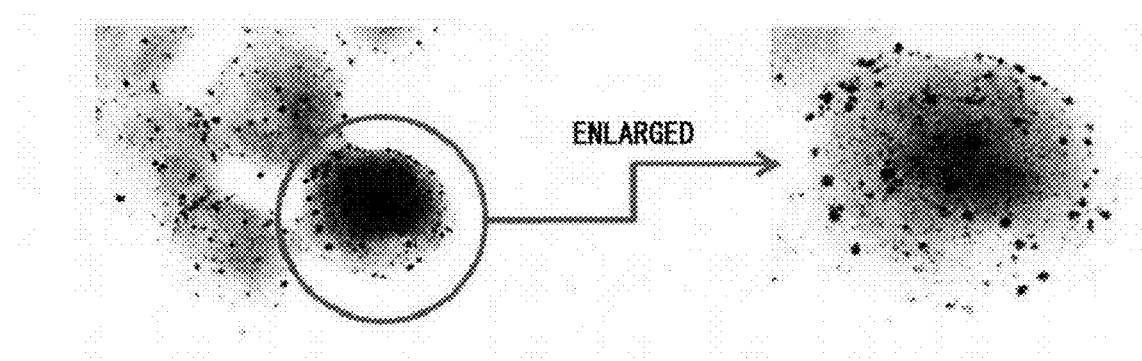
[Fig16]
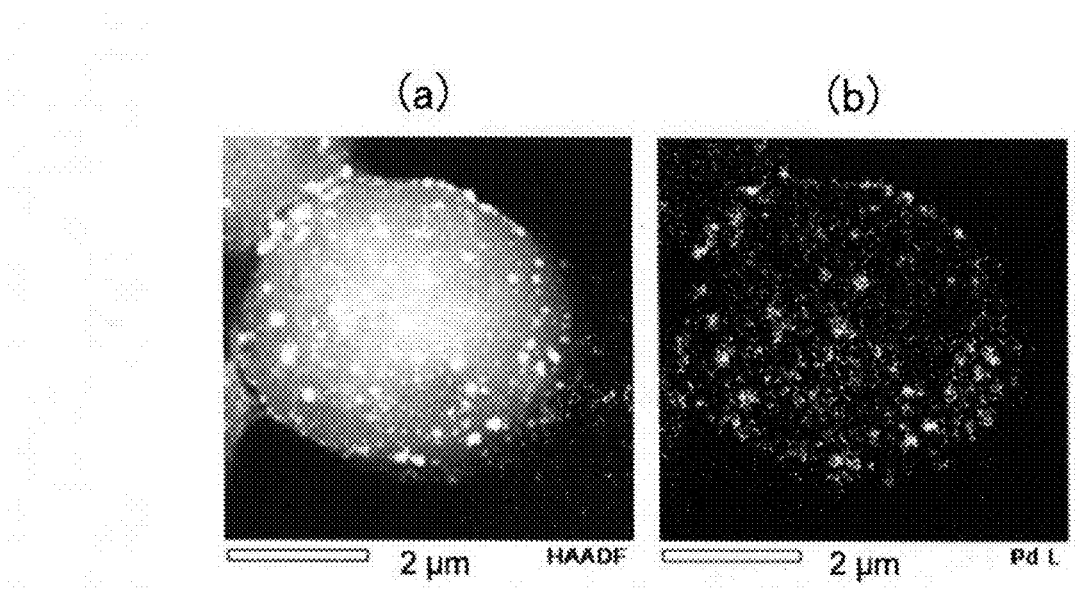
(a)     (b)

NOBLE METAL RECOVERY METHOD

TECHNICAL FIELD

The present invention relates to a noble metal recovery method.

BACKGROUND ART

A method of recovering metal from low-grade minerals, factory effluent, plants and the like by using microorganisms has been known. For example, Patent Literature 1 (Japanese Patent Laid-Open No. 2011-52315) discloses a method of recovering metal in which a yeast adsorbing specific metal ions is caused to adsorb the specific metal and then, the metal is recovered by using a chelating agent. Patent Literature 2 (Japanese Patent Laid-Open No. 11-77008) discloses a method of recovering metal after immersing fishery wastes in an aqueous solution containing lactic acid, a yeast and hydrocarbon and then, subjecting it to fermentation treatment. Patent Literature 3 (Japanese Patent Laid-Open No. 2004-33837) discloses a method of recovering metal in which a plant containing heavy metal is immersed in a culture solution containing lactic acid, a yeast and sugar so as to dissociate the heavy metal and then, the heavy metal is recovered by using the chelating agent. Moreover, Patent Literature 4 (Japanese Patent Laid-Open No. 2003-284556) and Patent Literature 5 (National Publication of International Patent Application No. 2009-538127) disclose a method of recovering metal by using a transformant such as a yeast in which a gene which codes a protein capturing or adsorbing the metal is transformed. The protein indicated in Patent Literature 4 is histidine polypeptide, and Patent Literature 4 indicates that it is recovered as metal ions. The protein indicated in Patent Literature 5 is phytochelatin synthetase or metallothionein, and it is indicated that the protein is recovered as a complex of metal and a protein.

However, since metal is recovered as metal ions in these methods, these methods require an operation of reducing the recovered metal ions and moreover, an operation of separating the metal ions from the complex with the protein in order to recover metal.

On the other hand, Patent Literature 6 (Japanese Patent Laid-Open No. 2007-113116) describes a method of recovering metal from metal oxides or metal hydroxides by causing iron-reducing bacteria to act. In this method, metal (reduced form) in a fungus body of the iron-reducing bacteria can be recovered.

However, since this method utilizes an iron reducing action of the iron-reducing bacteria, an electron donor is essential in a culture medium. There was also a problem that, since the fungus body of the iron-reducing bacteria is small, recovery of the bacteria from the solution is difficult.

Moreover, other than the iron-reducing bacteria, Non-Patent Literature 1 describes that a metabolite secreted by *Delftia acidovorans* isolated from the natural world to an outside of a cell reduces/deposits a trivalent Au ion in the culture solution to an Au nanoparticle, but reduction of noble metal ions by yeast and accumulation as metal in the fungus body has not been known so far.

CITATION LIST

Patent Literature

Patent Literature 1: Japanese Patent Laid-Open No. 2011-52315

Patent Literature 2: Japanese Patent Laid-Open No. 11-77008

Patent Literature 3: Japanese Patent Laid-Open No. 2004-33837

Patent Literature 4: Japanese Patent Laid-Open No. 2003-284556

Patent Literature 5: National Publication of International Patent Application No. 2009-538127

Patent Literature 6: Japanese Patent Laid-Open No. 2007-113116

Non-Patent Literature

Non-Patent Literature 1: Nature, Chemical Biology, 9, 241, 2013

SUMMARY OF THE INVENTION

Technical Problem

An object of the present invent ion is to provide a means for recovering noble metal ions as noble metal which is its reductant by using a reducing power of a yeast.

Solution to Problem

A method according to the present invention has a step of bringing a yeast and noble metal ions into contact with each other in a liquid containing the noble metal ions so as to accumulate the noble metal which is a reductant in a fungus body of the yeast.

Effects of the Invention

According to the present invention, the noble metal ions can be reduced by utilizing the yeast and recovered as the noble metal which is the reductant.

BRIEF DESCRIPTION OF THE DRAWINGS

FIG. 1 is a graph showing a reduction result of gold by *Saccharomyces cerevisiae* and *Debaryomyces hansenii*. A B strain is *Saccharomyces cerevisiae* (*Saccharomyces cerevisiae* BY4741 strain) and a D strain is *Debaryomyces hansenii* (*Debaryomyces hansenii* NITE BP-01780).

FIG. 2 is a TEM image of a yeast (B strain) after it is brought into contact with gold ions for 24 hours under presence of formate.

FIG. 3 is a graph showing a reduction result of palladium by *Saccharomyces cerevisiae* and *Debaryomyces hansenii*. The B strain is *Saccharomyces cerevisiae* (*Saccharomyces cerevisiae* BY4741 strain) and the D strain is *Debaryomyces hansenii* (*Debaryomyces hansenii* NITE BP-01780).

FIG. 4 is a TEM image of the yeast (B strain) after it is brought into contact with palladium ions for 24 hours under presence of formate.

FIG. 5 is a graph showing a reduction result of gold by a bakery yeast (budding yeast: *Saccahromyces cerevisiae* NBRC2044 strain).

FIG. 6 is a graph showing a reduction result of gold by a fission yeast (*Schizosaccharomyces pombe* FY15985 strain).

FIG. 7 is a graph showing a reduction result of gold by a miso yeast (*Zygosaccharomyces rouxii* NBRC1130 strain).

FIG. 8 is a diffraction diagram showing a result of powder X-ray diffraction measuring after drying (50° C., 48 hours)

the bakery yeast (budding yeast: *S. cerevisiae*) after being brought into contact with gold ions for 24 hours under presence of formate.

FIG. 9 is a TEM image of the bakery yeast (budding yeast: *S. cerevisiae*) after being brought into contact with gold ions for 24 hours under presence of formate and an image enlarging a part of the yeast.

FIGS. 10 are images showing an EDX analysis result of the bakery yeast (budding yeast: *S. cerevisiae*) after being brought into contact with gold ions for 24 hours under presence of formate, in which FIG. 10(*a*) is an image by HAADF, and FIG. 10(*b*) is an image after mapping of a gold element. A white portion in FIG. 10(*a*) indicates gold particles, and the white portion is mapped in FIG. 10(*b*).

FIG. 11 is a graph showing a reduction result of palladium by the bakery yeast (budding yeast: *Saccahromyces cerevisiae* NBRC2044 strain).

FIG. 12 is a graph showing a reduction result of palladium by the fission yeast (*Schizosaccharomyces pombe* FY15985 strain).

FIG. 13 is a graph showing a reduction result of palladium by the miso yeast (*Zygosaccharomyces rouxii* NBRC1130 strain).

FIG. 14 is a diffraction diagram showing a result of powder X-ray diffraction measuring after drying (50° C., 48 hours) the bakery yeast (budding yeast: *S. cerevisiae*) after being brought into contact with palladium ions for 24 hours under presence of formate.

FIG. 15 is a TEM image of the bakery yeast (budding yeast: *S. cerevisiae*) after being brought into contact with palladium ions for 24 hours under presence of formate and an image enlarging a part of the yeast.

FIG. 16 are images showing an EDX analysis result of the bakery yeast (budding yeast: *S. cerevisiae*) after being brought into contact with palladium ions for 24 hours under presence of formate, in which FIG. 16(*a*) is an image by HAADF, and FIG. 16(*b*) is an image after mapping of a palladium element. A white portion in FIG. 16(*a*) indicates palladium particles, and the white portion is mapped in FIG. 16(*b*).

DESCRIPTION OF EMBODIMENT

A method according to the present invention is a method having a step of bringing a yeast and noble metal ions into contact with each other in a liquid containing the noble metal ions so as to accumulate noble metal which is a reductant in a fungus body of the yeast. That is, the present invention is characterized in that the noble metal ions are recovered as noble metal by using a reducing power of the yeast.

Therefore, the yeast that can be used in the present invention may be any yeast as long as it is a yeast that can reduce noble metal ions in a fungus body. The yeast in the present invention is not limited to *Saccharomyces* but is used in a broader sense including other yeasts. The yeast that can be used in the present invention includes *Saccharomyces*, *Candida*, *Torulopsis*, *Zygosaccharorayces*, *Schizosaccharomyces*, *Pichia*, *Yarrowia*, *Hansenuia*, *Kluyveromyces*, *Debaryomyces*, *Geotrichum*, *Wickerhamia*, *Fellomyces*, and *Sporobolomyces*, and particularly, yeasts belonging to *Saccharomyces*, *Zygosaccharorayces*, *Schizosaccharomyces*, and *Debaryomyces* are preferable. The *Saccharomyces* yeast, which is representative of budding yeast, can include *S. bayanus*, *S. boulardii*, *S. bulderi*, *S. cariocanus*, *S. cariocus*, *S. cerevisiae*, *S. chevaiieri*, *S. dairenensis*, *S. ellipsoideus*, *S. florentinus*, *S. kluyveri*, *S. martiniae*, *S. monacensis*, *S. norbensis*, *S. paradoxus*, *S. pastordanus*, *S. spencerorum*, *S. turicensis*, *S. unisporus*, *S. uvarum* and *S. zonatus*, for example. *Zygosaccharorayces*, which is a salt-tolerant yeast and is separated from miso, soy sauce and the like, can include *Z. rouxii*, for example. *Schizosaccharomyces* yeast, which is a fission yeast, can include *S. cryophiius*, *S. japonicus*, *S. octosporus*, and *S. pombe*, for example. Moreover, *Debaryomyces hansenii* yeast deposited as a preferable yeast as NITE BP-01780 (Patent Microorganisms Depositary of the National Institute of Technology and Evaluation, #122, 2-5-8 Kazusa-kamatari, Kisarazu-shi, Chiba, Japan) is also exemplified.

Metal that can be recovered by the method according to the present invention is noble metal. Specifically, it can be gold and platinum group metal or more specifically, it can be gold, silver, platinum, palladium, rhodium, iridium, ruthenium, and osmium.

The contact between the noble metal ions of the noble metal and the yeast is performed in a liquid. The yeast may be viable bacteria or killed bacteria as long as its reducing function is exerted. The liquid may be any environment in which the function of the yeast is exerted. For example, it may be only water or can be a liquid in which only a pH adjuster such as potassium hydrogenphosphate and/or sodium chloride (sodium chloride derived from physiological saline used for suspension of the yeast or sodium chloride for isotonicity) is added to water. The liquid is a solution (added solution) to which an electron donor is artificially added or can also be a solution (additive-free solution) to which the electron donor is not artificially added. The electron donor can be low-molecular organic acids and/or salts thereof, alcohols or hydrogen gas, for example. The organic acids can be aliphatic carboxylic acids with a carbon number of 1 to 7 such as formic acid, acetic acid, and lactic acid, aromatic carboxylic acids having a carboxyl group with a carbon number of 1 to 7 such as benzoic acid, pyruvic acid, and oxocarboxylic acid, for example. The alcohols can be aliphatic alcohols with a carbon number of 1 to 7 such as methanol and ethanol, for example. Addition of these electron donors contributes to reduction of the noble metal ions and can increase a reducing amount (reducing power) of the noble metal ions. In the present invention, a final acceptor of electrons supplied from the electron donors is considered to be metal ions and thus, addition of the electron acceptor is not indispensable.

The liquid does not necessarily require nutrients necessary for growth of the yeast but it can be a liquid containing required minimum nutrients (nitrogen source or carbon source) for growth of the yeast. Such nutrients are nutrients used for culturing yeast and can be sucrose, glucose, lactose, yeast extract, meat extract, bouillon, polypeptone or peptone, for example. If the nutrients are contained, the liquid to be brought into contact with the yeast is prepared by adding these nutrients in a liquid containing the noble metal ions or by adding a liquid containing the noble metal ions to be recovered in a solution containing these nutrients. The liquid containing the nutrients can be a YPD medium specified for the yeast or a bouillon medium which is a general-purpose medium.

The liquid containing the noble metal ions can be prepared from a recovery object by a known method. The preparing method is a method of suspending it in water and applying acid treatment as necessary in the case of soil or a method of applying acid treatment and applying filtering or neutralization treatment as necessary in the case of a mineral or an alloy, for example. The recovery object only needs to be an object that can be taken out as noble metal ions, and whether it is salt or metal such as an alloy or whether it is a liquid or a solid does not matter and is not particularly limited as long as the aforementioned noble metal or noble metal ions are contained. The liquid containing the noble metal ions can contain non-noble metal other than the aforementioned noble metal or non-noble metal ions.

The pH or a temperature of the liquid to be brought into contact with the yeast is a matter that can be set as appropriate by those skilled in the art. The pH of the liquid is preferably neutral at approximately 7 to mildly acidic at approximately pH5, and the temperature is preferably 25 to 35° C. Contact time is varied depending on a fungus body density of the yeast or concentration of the noble metal ions but it is approximately 1 hour to 48 hours, and by bringing the noble metal ions into contact with the yeast for such time, the noble metal ions are reduced in the fungus body of the yeast and is accumulated in the fungus body of the yeast as noble metal (particle). Moreover, it is preferable to shake the liquid during contact with the yeast. That is because a moving speed of the noble metal ions in the liquid to be diffused over the surface of the yeast increases.

The noble metal ion concentration of the liquid to be contacted with the yeast is also a matter that can be set as appropriate by those skilled in the art. The noble metal ion concentration is varied depending on the fungus body concentration of the yeast but it is approximately 0.01 to 100 mmol/l and is preferably 0.1 to 10 mmol/l. An added amount of the electron donor can be also set as appropriate. The added amount of the electron donor is varied depending on the metal type or a fungus body number, but in the case of the aforementioned noble metal ion concentration, the concentration in the liquid to be contacted with the yeast is approximately 0.01 to 1000 mmol/l and it is approximately the same degree as the noble metal ion concentration or more or preferably approximately 10 times thereof.

The noble metal reduced is recovered as noble metal particles (noble metal crystals) by destroying the fungus body of the yeast after being brought into contact with the noble metal ions. Since a density of the recovered metal particles is high, they precipitate in the solution in which the fungus bodies have been destroyed, and the precipitates are easily recovered by a known method. Alternatively, the noble metal may be recovered from the fungus body after the fungus body of the yeast is recovered. For example, a method of recovering as the noble metal particles or noble metal mass by burning the recovered yeast is exemplified.

As described above, since the method of the present invention is a method of recovering the noble metal ions in the fungus body of the yeast as metal (particle) by using the reducing power of the yeast, recovery from the yeast is easy. Moreover, since the yeast fungus body is larger than the fungus body of iron-reducing bacteria (the yeast fungus body is approximately 5 microns with respect to approximately 1 micron of the iron-reducing fungus body), solid-liquid separation of the fungus body is easier than the fungus body of the iron-reducing bacteria.

The present invention will be further described below on the basis of the following examples but it is needless to say that the present invention is not limited to the following examples.

EXAMPLE 1

*Saccharomyces cerevisiae* (BY4741 strain: B strain) which is a representative bacteria of a yeast and *Debaryomyces hansenii* (D strain) which is a cadmium-resistant yeast were used. This *Debaryomyces hansenii* was isolated as follows, and deposited as NITE BP-01780 (Patent Microorganisms Depositary of the National Institute of Technology and Evaluation, #122, 2-5-8 Kazusa-kamatari, Kisarazu-shi, Chiba-ken, Japan, which is an international depositary agency on Dec. 6, 2013.

[Isolation of *Debaryomyces hansenii* (D Strain)]

The yeast was screened from fermented salt, food products such as various sake lees/miso and the like. The isolated source sample was suspended in sterilized water, the suspension was applied on a YPD (2% glucose, 0.5% yeast extract, and 0.5% peptone) plate medium containing 13% of NaCl and cultured at 30° C. for 48 hours and then, growing colonies were isolated. From the isolated strains, the yeast was screened by microscopic visualization. The obtained salt-tolerant yeast strain was inoculated into the YPD liquid medium containing 200 μM of cadmium chloride and then, stationarily cultured at 30° C. A fungus-body cadmium content of the strain having grown up to 72 hours was measured, and the strain containing cadmium in an amount larger than the aforementioned *Saccharomyces cerevisiae*, B strain was isolated.

(Recovery of Gold)

The aforementioned two strains of yeast were inoculated into the YPD medium, respectively, and then, stationaliry cultured at 30° C. for 48 hours. After the cultured fungus bodies were recovered, the yeast was added to an aqueous solution of gold chloride containing 1.0 mmol/m$^3$ of gold ions (Au$^{3+}$) so that the fungus body concentration of the B strain becomes 0.8×10$^8$ cells/ml and the fungus body concentration of the D strain becomes 1.0×10$^8$ cells/ml, respectively. After the addition of the yeast, it was left at rest at 30° C., and a change of the gold concentration of the solution and a color tone change of the solution were examined. Moreover, similar experiments were conducted for the case in which, after sodium formate as the electron donor was added so as to be 50 mmol/m$^3$ and the case in which a hydrogen gas was supplied into the solution. The results are illustrated in FIG. 1. Moreover, the yeast after contact for 24 hours under presence of sodium formate was photographed by using TEM (Transmission Electron Microscope). The result is illustrated in FIG. 2.

As can be seen from FIG. 1, regardless of presence or absence of the electron donor, the pH was kept at 6.5 to 6.6 for all the strains, while Au concentration of the solution lowered. In all the systems, the color of the solution after contact for 24 hours changed from pale purple to pink from yellow or lemon yellow before start of the experiments. A phenomenon that superfine particles of the metal absorb light with a specific wavelength (plasmon absorption) is well-known, and a color change is observed due to this phenomenon if metal particles are present, and the color change is varied depending on a size or a type of the metal fine particles. If the plasmon absorption occurs, it is generally known that gold nanoparticles exhibit "purple to pink (the color changes in accordance with a particle diameter)". As a result, it was determined that the metal fine particles were generated in the solution. Moreover, as illustrated in FIG. 2, the Au metal fine particles were confirmed also from the TEM images in the fungus body of the yeast not outside the fungus body of the yeast. From these facts, it is determined that these yeasts reduce the Au ion and accumulate Au in the fungus body regardless of presence or absence of the electron donor.

(Recovery of Palladium)

Into the aqueous solution of palladium chloride with the concentration of 1.0 mmol/l, the yeast with the same concentration as above was added, and the experiment similar to the case of gold was conducted by using sodium formate and sodium lactate as the electron donors. The result is illustrated in FIG. 3. Moreover, TEM images of the yeast after contact for 24 hours under the presence of sodium formate are shown in FIG. 4. The color of the solution was yellow or lemon yellow in all the systems but changed to black after approximately 2.5 hours under the presence of sodium formate and after approximately 4 hours under the presence of sodium lactate for the D strain. For the B strain, too, the color changed to black after 24 hours. It is known that nanoparticles of palladium exhibit black color by the plasmon absorption. From these facts, it was confirmed that the yeast reduces Pd ion and accumulates Pd in the fungus body under the presence of the electron donor.

EXAMPLE 2

Subsequently, the similar experiments were conducted by using three strains of yeast different from the B strain and D strain. The *Saccharomyces cerevisiae* NBRC 2044 strain as a bakery yeast, the *Schizosaccharomyces pombe* FY15985 strain as a fission yeast, and the *Zygosaccharomyces rouxii* NBRC1130 strain as miso yeast were used.

(Recovery of Gold)

The yeast was added to an aqueous solution of gold chloride containing 1.27 mmol/m$^3$ of gold ions (Au$^{3+}$) so that the fungus body concentration becomes 1.5×10$^{15}$ cells/ml. After the addition of the yeast, it was left at rest at 30° C., and a change of the gold concentration of the solution and a color tone change of the solution were examined. Moreover, similar experiments were conducted for the case in which sodium formate was added as the electron donor so as to be 50 mmol/m$^3$. The results are illustrated in FIGS. 5 to 7. Percentages in the figures indicate lowering degrees of the concentration after 24 hours. During this period, the pH of the solution was kept at 6.5 to 6.7, but the gold ion concentration of the solution lowered. Moreover, the color of the solution changed from pink to purple under the presence of sodium formate, and reduction of the gold ions were recognized. In the case in which only sodium formate was added as control, remarkable lowering of the gold ion concentration was not observed within time immediately after the addition of the yeast when bio-reduction by the yeast remarkably occurred. It was confirmed that chemical reduction did not occur during this period (not shown). On the other hand, lowering of the gold ion concentration was recognized even in the case in which sodium formate was not added, and it is considered that not only reduction but also adsorption and absorption of ions occur under non-presence of the electron donor. Moreover, as the result of powder X-ray diffraction of the bakery yeast after being brought into contact with gold ions under the presence of sodium formate, it was confirmed that the gold ions were reduced and gold (metal) was produced (see FIG. 8). Accumulation of the gold particles in the yeast fungus body was also confirmed from the TME images of the yeast and EDX mapping (see FIGS. 9 and 10).

(Recovery of Palladium)

Into the aqueous solution of palladium chloride with the concentration of 1.2 mmol/m$^3$ of palladium ions (Pd$^{2+}$), the yeast was added so that the fungus body concentration becomes 1.5×10$^{14}$ cells/ml (however, the bakery yeast was 1.5×10$^{15}$ cells/ml). After the addition of the yeast, it was left at rest at 30° C., and a change of the palladium concentration of the solution and a color tone change of the solution were examined. Moreover, the similar experiments were conducted for the case in which the sodium formate as an electron donor was added so as to be 50 mmol/m$^3$. The results are illustrated in FIGS. 11 to 13. Percentages in the figures indicate lowering degrees of the concentration after 24 hours. During this period, the pH of the solution was kept at 6.5 to 6.7, but the palladium ion concentration of the solution lowered. The color of the solution changed to black under presence of sodium formate, and reduction of palladium ions was recognized. In the case in which sodium formate as control was added, remarkable lowering of the palladium ion concentration was not observed within time immediately after the addition of the yeast when bio-reduction by the yeast remarkably occur. It was confirmed that chemical reduction did not occur during this period (not shown). On the other hand, lowering of the palladium ion concentration was also recognized even if sodium formate was not added, and it is considered that adsorption and absorption of ions rather than reduction occur under non-presence of the electron donor in these yeasts. Moreover, as the result of powder X-ray diffraction of the bakery yeast after being brought into contact with palladium ions under the presence of sodium formate, it was confirmed that the palladium ions were reduced and palladium (metal) was produced (see FIG. 14). Accumulation of the palladium particles in the yeast fungus body was also confirmed from the TME images of the yeast and EDX mapping (see FIGS. 15 and 16).

From these results, not limited to the yeast B strain and D strain as well as the fission yeast under the non-presence of the electron donor, various yeasts represented by a yeast widely used for fermentation such as bread, miso and the like can be used for reduction of noble metal under presence of the electron donor.

INDUSTRIAL APPLICABILITY

The present invention provides a method of recovering noble metal ions in a solution as noble metal by using a yeast.

[Supplementation Based on Rule 26 Jan. 19, 2015]

| | | |
|---|---|---|
| 0-1 | Form PCT/RO/134[SAFE] Indications relating to the deposited microorganism or other biological material | |
| 0-1-1 | (PCT Rule 13(2)) were made by those identified on the right. | JPO-PAS 1222 |
| 0-2 | International Application Number | |
| 0-3 | Document Number on Applicant or Attorney | 13PCT11704 |
| 1 | The indications below relate to the microorganism or other biological material described in Detailed Description of the Invention. | |
| 1-1 | Paragraph Number | 0014 0024 |
| 1-3 | Indications of depositary | |
| 1-3-1 | Name of depositary institution | NPMD Patent Microorganisms Depositary (NPMD) |
| 1-3-2 | Address of depositary institution | #122, 2-5-8 Kazusa-kamatari, Kisarazu-shi, Chiba, Japan, 292-0818 |
| 1-3-4 | Date of deposit | Dec. 6, 2013 (Dec. 12, 2013) |
| | Accession Number | NPMD NITE BP-01780 |
| 1-5 | Designated Nations on This Indication | All Designated Nations |

-continued

| For receiving Office use only | |
|---|---|
| 0-4 | This sheet was received with the international application (Yes/No) |
| 0-4-1 | Authorized officer |
| For International Bureau use only | |
| 0-5 | This sheet was received by the International Bureau on: |
| 0-5-1 | Authorized officer |

The invention claimed is:

1. A noble metal recovery method comprising:
providing a liquid containing noble metal ions;
adding an electron donor and a yeast into the liquid to bring the yeast in contact with the noble metal ions to reduce the noble metal ions; and
accumulating the noble metal in a fungus body of the yeast,
wherein the electron donor is selected from an organic acid, a salt thereof, an alcohol and hydrogen gas.

2. The noble metal recovery method according to claim 1, wherein
the noble metal ions are one or more ions selected from a group consisting of gold, silver, platinum, palladium, rhodium, iridium, ruthenium, and osmium.

3. The noble metal recovery method according to claim 1, wherein
contact is made with one or more of yeasts among yeasts of Saccharomyces, Zygosaccharomyces, Schizosaccharomyces, and Debaryomyces.

4. The noble metal recovery method according to claim 1, wherein the electron donor is selected from aliphatic carboxylic acids having a carbon number of 1 to 7 and salts thereof, aromatic carboxylic acids having a carboxyl group having a carbon number of 1 to 7 and salts thereof, aliphatic alcohols having a carbon number of 1 to 7, and hydrogen gas.

5. The noble metal recovery method according to claim 1, wherein the electron donor is selected from formic acid, acetic acid, lactic acid, benzoic acid, pyruvic acid, oxocarboxylic acid, salts thereof, methanol, ethanol and hydrogen gas.

* * * * *